(12) United States Patent
Estabrook et al.

(10) Patent No.: US 6,274,963 B1
(45) Date of Patent: Aug. 14, 2001

(54) METHODS AND DEVICES FOR CONTROLLING THE VIBRATION OF ULTRASONIC TRANSMISSION COMPONENTS

(75) Inventors: Brian Estabrook, Foxboro, MA (US); Scott Kellogg, Esmond, RI (US); Stephen J. Alam, North Attleboro, MA (US)

(73) Assignee: Ethicon Endo-Surgery, Inc., Cincinnati, OH (US)

(*) Notice: Subject to any disclaimer, the term of this patent is extended or adjusted under 35 U.S.C. 154(b) by 0 days.

(21) Appl. No.: 09/386,740

(22) Filed: Aug. 31, 1999

Related U.S. Application Data

(62) Division of application No. 08/848,064, filed on Apr. 28, 1997, now abandoned.

(51) Int. Cl.[7] .................................................. H01L 41/08
(52) U.S. Cl. ................................................... 310/316.02
(58) Field of Search ..................... 310/316.01, 316.02; 318/116

(56) References Cited

U.S. PATENT DOCUMENTS

| 2,845,072 | 7/1958 | Shafer . |
| 3,053,124 | 9/1962 | Balamuth et al. . |
| 3,433,226 | 3/1969 | Boyd . |
| 3,636,943 | 1/1972 | Balamuth . |
| 3,657,056 | 4/1972 | Winston et al. . |
| 3,792,701 | 2/1974 | Kloz et al. . |
| 3,819,961 | 6/1974 | Bourgeois et al. . |
| 3,842,340 | 10/1974 | Brandquist . |
| 3,886,495 | * 5/1975 | Sexton et al. .................... 340/18 LD |
| 3,967,143 | 6/1976 | Watanabe et al. . |
| 4,169,984 | 10/1979 | Parisi . |
| 4,223,676 | 9/1980 | Wuchinich et al. . |

(List continued on next page.)

FOREIGN PATENT DOCUMENTS

| 77 05 069 | 2/1977 | (DE) . |
| 2032501 | 12/1989 | (DE) . |
| 19534618.1 | 3/1997 | (DE) . |
| 0 765 637A | 2/1997 | (EP) . |
| 76 18881 | 6/1976 | (FR) . |
| 61-128954 | 6/1986 | (JP) . |
| 63-61609 | 11/1988 | (JP) . |
| 8-275948 | 10/1996 | (JP) . |
| 8-275949 | 10/1996 | (JP) . |
| 8-275951 | 10/1996 | (JP) . |
| 9-98980 | 4/1997 | (JP) . |

Primary Examiner—Mark O. Budd
(74) Attorney, Agent, or Firm—Verne E. Kreger, Jr.

(57) ABSTRACT

A transducer assembly in accordance with the present invention includes at least one transducer element having a first end and a second end. A first electrode is coupled to the first end and a segmented electrode is coupled to the second end. The segmented electrode is adapted to allow the transducer element to be simultaneously driven by a plurality of electric signals. A generator in accordance with the present invention includes a frequency control loop to generate an electrical signal having a desired level of vibration. A first amplifier having a selected gain receives the electrical signal from the frequency control loop. The first amplifier generates a first output signal to drive the transducer element. A second amplifier having a selected gain receives the electrical signal from the frequency control loop. The second amplifier generates a second output signal to drive the transducer element.

8 Claims, 7 Drawing Sheets

U.S. PATENT DOCUMENTS

| | | |
|---|---|---|
| 4,375,961 | 3/1983 | Brooks . |
| 4,522,206 | 6/1985 | Whipple et al. . |
| 4,587,958 * | 5/1986 | Noguchi et al. ............... 310/316.01 |
| 4,655,216 | 4/1987 | Tischer . |
| 4,713,571 * | 12/1987 | Suzuki et al. ................ 310/316.02 |
| 4,723,545 | 2/1988 | Nixon et al. . |
| 4,825,865 | 5/1989 | Zelman . |
| 4,832,683 | 5/1989 | Idemoto et al. . |
| 4,888,565 | 12/1989 | Littleford et al. . |
| 4,961,424 | 10/1990 | Kubota et al. . |
| 4,965,532 * | 10/1990 | Sakurai ........................ 310/316.01 |
| 5,026,387 * | 6/1991 | Thomas ........................ 310/316.01 |
| 5,167,725 | 12/1992 | Clark et al. . |
| 5,180,363 | 1/1993 | Idemoto et al. . |
| 5,263,957 | 11/1993 | Davison . |
| 5,322,055 | 6/1994 | Davison et al. . |
| 5,324,299 | 6/1994 | Davison et al. . |
| 5,425,704 | 6/1995 | Sakurai et al. . |
| 5,630,420 | 5/1997 | Vaitekunas . |
| 5,634,466 | 6/1997 | Gruner . |
| 5,653,721 | 8/1997 | Knodel et al. . |
| 5,688,235 * | 11/1997 | Sakurai et al. . |
| 5,720,710 * | 2/1998 | Tachibana et al. . |
| 5,739,621 * | 4/1998 | Atsuta et al. ................. 310/316.02 |
| 5,827,204 * | 10/1998 | Grandia et al. . |
| 5,859,490 * | 1/1999 | Saya ............................. 310/316.02 |
| 5,897,569 * | 4/1999 | Kellogg et al. ............... 310/316.01 |
| 5,986,385 * | 11/1999 | Atsuta .......................... 310/316.02 |
| 6,037,701 * | 3/2000 | Atsuta .......................... 310/316.02 |
| 6,121,714 * | 9/2000 | Atsuta .......................... 310/316.02 |

\* cited by examiner

FIG. 9
I CURRENT CONTROL

FIG. 11
III VOLTAGE CONTROL

FIG. 10
II SERIES IMPEDENCE CONTROL

FIG. 12
IV PHASE CONTROL

METHODS AND DEVICES FOR CONTROLLING THE VIBRATION OF ULTRASONIC TRANSMISSION COMPONENTS

This is a Divisional of prior application Ser. No. 08/848,064, filed Apr. 28, 1997, now abandoned.

FIELD OF THE INVENTION

The present invention generally relates to ultrasonic devices. More particularly, the present invention relates to methods and devices for controlling the vibration of ultrasonic transmission components by applying a plurality of signals to a transducer element through the use of a segmented electrode.

BACKGROUND OF THE INVENTION

Ultrasonic transmission devices are frequently used in a variety of applications, such as, for example, surgical operations and procedures. Ultrasonic surgical devices usually include a transducer assembly that converts electrical energy into vibrational motion at ultrasonic frequencies. The vibrational motion of the transducer assembly is transmitted to vibrate a distal end of a transmission component. The distal end of the transmission component, may transmit the ultrasonic energy to selected tissue of a patient, for example, to cut, dissect, and cauterize the tissue.

The ultrasonic vibration is induced in the transmission component by exciting one or more piezoelectric elements of the transducer assembly by an electrical signal. The electrical signal is transmitted to electrodes that are coupled to the piezoelectric elements. The electrodes are typically disposed on each side of the piezoelectric elements. When the electrical signal is transmitted to the electrodes, an electric field is established across the piezoelectric elements causing the piezoelectric elements to generate a mechanical standing wave at a frequency approximately equal to the frequency of the electrical excitation signal.

One of the problems associated with ultrasonic surgical instruments is uncontrolled and undampened vibrations of the transmission component as well as material fatigue resulting therefrom. Conventional mechanical dampening has been used to reduce undesired vibrations of transmission components of ultrasonic surgical instruments. For example, silicone rings have been disposed near nodes of the transmission component to reduce undesired vibration. However, the silicone rings can decrease the performance of the transmission component, dissipate desirable ultrasonic energy, increase the design time of the transmission component, and increase the heating of the transmission component. In addition, the distribution of current flow through the transducer assembly cannot be sensed or controlled.

Accordingly, there is a need for improved devices and methods to control the vibration of ultrasonic transmission components to allow the desired frequency to pass to the distal end of the transmission components. It would also be desirable to dampen the undesired vibration of the vibrational elements of the transducer assembly.

SUMMARY OF THE INVENTION

In view of the above, devices and methods are provided to control the vibration of ultrasonic transmission components. The devices and methods can undesired frequencies of vibration, such as, for example, non-fundamental modes, in vibrational elements of a transducer assembly and can control the electrical field distributed across the vibrational elements. The electrical properties (i.e., current, voltage, impedance, and phase) of the vibrational elements of the transducer assembly can be continuously monitored and adjusted to provide a desired vibrational frequency. The vibration of the transducer assembly can be controlled by applying a plurality of drive signals to a transducer element by the use of a segmented electrode.

The devices and methods can also introduce non-fundamental modes of vibration. The introduction of non-fundamental modes can allow more efficient delivery of power at the fundamental frequency of the transducer assembly. In addition, introduction of the non-fundamental modes of vibration can enhance tissue effects.

The devices and methods further allow longer and narrower transmission components (i.e., blades) to be utilized. Furthermore, mechanical dampening can be reduced, resulting in increased efficiency of the ultrasonic energy transmitted to the transmission component. The devices and methods also increase life expectancy of the transmission components.

An ultrasonic surgical device in accordance with the present invention includes a transducer assembly adapted to vibrate at an ultrasonic frequency in response to electrical energy. The transducer assembly includes at least one vibrational element and a segmented electrode. The segmented electrode has a plurality of input leads and plurality of contact regions. The plurality of contact regions are in electrical communication with the at least one vibrational element. A transmission component is adapted to receive the ultrasonic vibration from the transducer assembly and to transmit the ultrasonic vibration from a first end to a second end of the transmission component.

A transducer assembly in accordance with the present invention includes a transducer assembly comprising at least one transducer element having a first end and a second end. A first electrode is coupled to the first end and a segmented electrode is coupled to the second end. The segmented electrode is adapted to allow the transducer element to be simultaneously driven by a plurality of electric signals.

A generator in accordance with the present invention includes a frequency control loop to generate an electrical signal having a desired level of vibration. A first amplifier having a selected gain receives the electrical signal from the frequency control loop. The first amplifier generates a first output signal to drive the transducer element. A second amplifier having a selected gain receives the electrical signal from the frequency control loop. The second amplifier generates a second output signal to drive the transducer element.

It is to be understood that both the foregoing general description and the following detailed description are exemplary and explanatory and are intended to provide further explanation of the invention as claimed.

The invention, together with attendant advantages, will best be understood by reference to the following detailed description of the preferred embodiments of the invention, taken in conjunction with the accompanying drawings.

DESCRIPTION OF THE PREFERRED EMBODIMENTS

Before explaining the present invention in detail, it should be noted that the invention is not limited in its application or use to the details of construction arrangement of parts illustrated in the accompanying drawings and description, because the illustrative embodiments of the invention may be implemented or incorporated in other embodiments, variations and modifications, and may be practiced or carried out in various ways. Furthermore, unless otherwise indicated, the terms and expressions employed herein have been chosen for the purpose of describing the illustrative embodiments of the present invention for the convenience of the reader and are not for the purpose of limitation.

Figure 1:
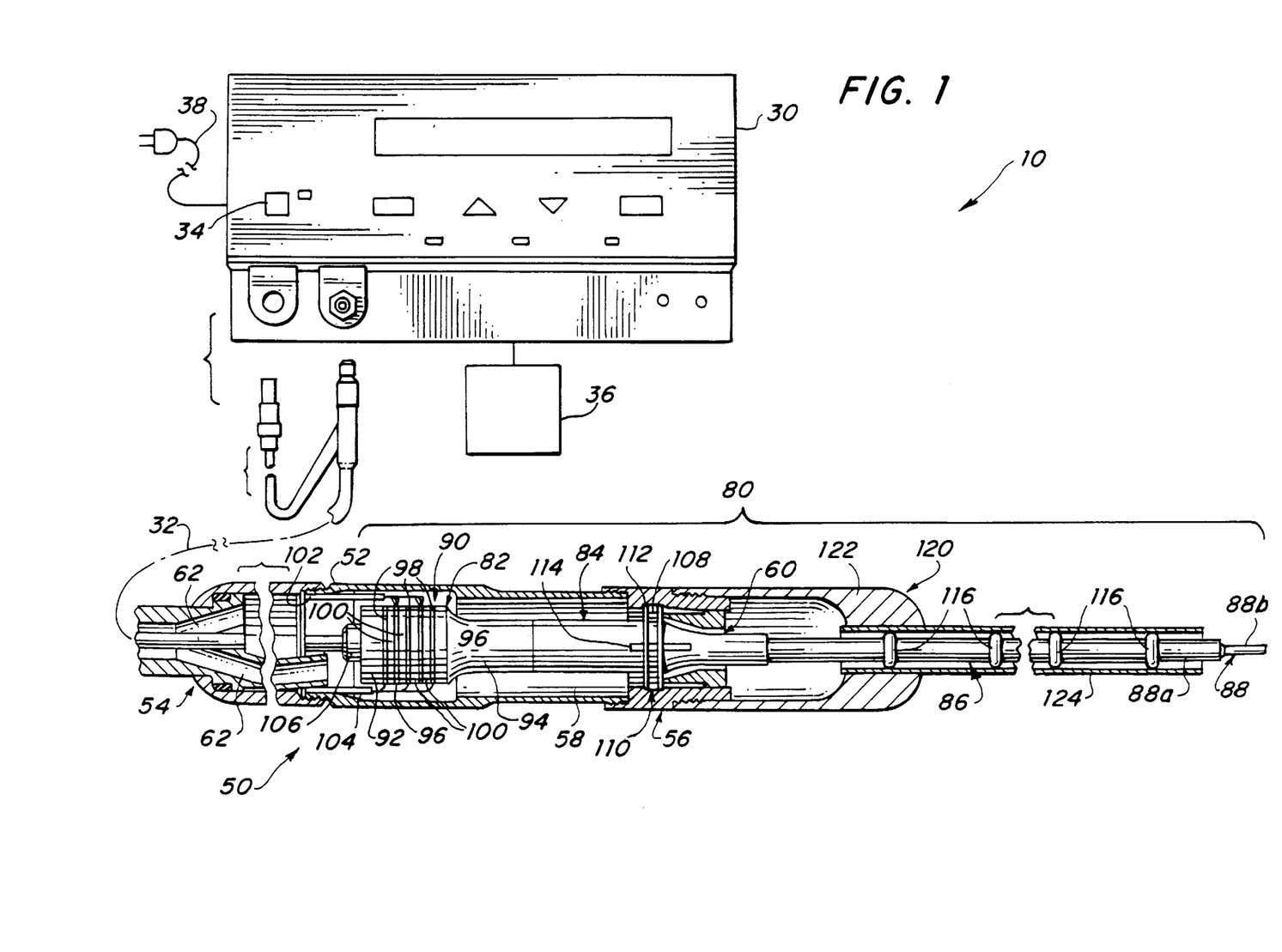
FIG. 1 is a fragmentary view and in partial cross-section of an embodiment of a surgical system according to the present invention.

Referring now to FIG. 1, a presently preferred embodiment of a surgical system 10 is illustrated. The surgical system 10 generally includes a generator 30, a handpiece assembly 50, and an acoustic or transmission assembly 80. The generator 30 sends an electrical signal through a cable 32 at a selected amplitude, frequency, and phase determined by a control system of the generator 30. As will be further described, the signal causes one or more piezoelectric elements of the acoustic assembly 80 to expand and contract, thereby converting the electrical energy into mechanical motion. The mechanical motion results in longitudinal waves of ultrasonic energy that propagate through the acoustic assembly 80 in an acoustic standing wave to vibrate the acoustic assembly 80 at a selected frequency and amplitude. An end effector 88 at the distal. end of the acoustic assembly 80 is placed in contact with tissue of the patient to transfer the ultrasonic energy to the tissue. The cells of the tissue in contact with the end effector 88 of the acoustic assembly 80 will move with the end effector 88 and vibrate.

As the end effector 88 couples with the tissue, thermal energy or heat is generated as a result of internal cellular friction within the tissue. The heat is sufficient to break protein hydrogen bonds, causing the highly structured protein (i.e., collagen and muscle protein) to denature (i.e., become less organized). As the proteins are denatured, a sticky coagulum forms to seal or coagulate small blood vessels when the coagulum is below 100° C. Deep coagulation of larger blood vessels results when the effect is prolonged.

The transfer of the ultrasonic energy to the tissue causes other effects including mechanical tearing, cutting, cavitation cell disruption, and emulsification. The amount of cutting as well as the degree of coagulation obtained varies with the vibrational amplitude of the end effector 88, the amount of pressure applied by the user, and the sharpness of the end effector 88. The end effector 88 of the acoustic assembly 80 in the surgical system 10 tends to focus the vibrational energy of the system 10 onto tissue in contact with the end effector 88, intensifying and localizing thermal and mechanical energy delivery.

As illustrated in FIG. 1, the generator 30 includes a control system integral to the generator 30, a power switch 34, and a triggering mechanism 36. The power switch 34 controls the electrical power to the generator 30, and when activated by the triggering mechanism 36, the generator 30 provides energy to drive the acoustic assembly 80 of the surgical system 10 at a predetermined frequency and to drive the end effector 88 at a predetermined vibrational amplitude level. The generator 30 may drive or excite the acoustic assembly 80 at any suitable frequency.

When the generator 30 is activated via the triggering mechanism 36, electrical energy may be continuously applied by the generator 30 to a transducer assembly 82 of the acoustic assembly 80. The electrical energy supplied to the acoustic assembly 80 will cause the distal end to vibrate longitudinally in the range of, for example, approximately 20 kHz to 100 kHz, and preferably in the range of about 54 kHz to 56 kHz, and most preferably at about 55.5 kHz. The amplitude of the acoustic vibrations at the end effector 88 can be controlled by, for example, controlling the amplitude of the electrical signal applied to the transducer assembly 82 of the acoustic assembly 80 by the generator 30 as further described below.

As noted above, the triggering mechanism 36 of the generator 30 allows a user to activate the generator 30 so that electrical energy may be continuously supplied to the acoustic assembly 80. In one embodiment, the triggering mechanism 36 preferably comprises a foot-activating switch that is detachably coupled or attached to the generator 30 by a cable or cord. In another embodiment, a hand switch may be incorporated in the handpiece assembly 50 to allow the generator 30 to be activated by a user.

The generator 30 also has a power line 38 for insertion in an electrosurgical unit or conventional electrical outlet. It is contemplated that the generator 30 may also be powered by a direct current (DC) source, such as a battery.

Referring still to FIG. 1, the handpiece assembly 50 includes a multi-piece housing or outer casing 52 adapted to isolate the operator from the vibrations of the acoustic assembly 80. The housing 52 is preferably cylindrically shaped and is adapted to be held by a user in a conventional manner, but may be any suitable shape and size which allows it to be grasped by the user. While a multi-piece housing 52 is illustrated, the housing 52 may comprise a single or unitary component.

The housing 52 of the handpiece assembly 50 is preferably constructed from a durable plastic, such as Ultem®. It is also contemplated that the housing 52 may be made from a variety of materials including other plastics (i.e. high impact polystyrene or polypropylene).

Referring still to FIG. 1, the handpiece assembly 50 generally includes a proximal end 54, a distal end 56, and centrally disposed axial opening or cavity 58 extending longitudinally therein. The distal end 56 of the handpiece assembly 50 includes an opening 60 configured to allow the acoustic assembly 80 of the surgical system 10 to extend therethrough, and the proximal end 54 of the handpiece assembly 50 is coupled to the generator 30 by a cable 32. The cable 32 may include ducts or vents 62 to allow air to be introduced into the handpiece assembly 50 to cool the transducer assembly 82 of the acoustic assembly 80.

Referring still to FIG. 1, the acoustic assembly 80 generally includes a transducer stack or assembly 82 and a transmission component or working member. The transmission component may include a mounting device 84, a transmission rod or waveguide 86, and an end effector or applicator 88. The transducer assembly 82, mounting device 84, transmission rod 86, and the end effector 88 are preferably acoustically tuned such that the length of each component is an integral number of one-half system wavelengths (nλ2) where the system wavelength λ is the wavelength of a preselected or operating longitudinal vibration frequency f of the acoustic assembly 80. It is also contemplated that the acoustic assembly 80 may incorporate any suitable arrangement of acoustic elements. For example, the acoustic assembly 80 may comprise a transducer assembly and an end effector (i.e., the acoustic assembly 80 may be configured without a mounting device and a transmission rod).

The transducer assembly 82 of the acoustic assembly 80 converts the electrical signal from the generator 30 into mechanical energy that results in longitudinal vibratory motion of the end effector 88 at ultrasonic frequencies. When the acoustic assembly 80 is energized, a vibratory motion standing wave is generated through the acoustic assembly 80. The amplitude of the vibratory motion at any point along the acoustic assembly 80 depends on the location along the acoustic assembly 80 at which the vibratory motion is measured. A minimum or zero crossing in the vibratory motion standing wave is generally referred to as a node (i.e., where axial motion is usually minimal and radial motion is usually small), and an absolute value maximum or peak in the standing wave is generally referred to as an antinode. The distance between an antinode and its nearest node is one-quarter wavelength (λ4).

As shown in FIG. 1, the transducer assembly 82 of the acoustic assembly 80, which is known as a "Langevin stack," generally includes a transduction portion 90, a first resonator 92, and a second resonator 94. The transducer assembly 82 is preferably an integral number of one-half system wavelengths (nλ/2) in length. It is to be understood that the present invention may be alternatively configured to include a transducer assembly comprising a magnetostrictive, electromagnetic or electrostatic transducer.

The distal end of the first resonator 92 is connected to the proximal end of transduction section 90, and the proximal end of the second resonator 94 is connected the distal end of transduction portion 90. The first and second resonators 92 and 94 are preferably fabricated from titanium, aluminum, steel, or any other suitable material. The first and second resonators 92 and 94 have a length determined by a number of variables, including the thickness of the transduction section 90, the density and modulus of elasticity of material used in the resonators 92 and 94, and the fundamental frequency of the transducer assembly 82. The second resonator 94 may be tapered inwardly from its proximal end to its distal end to amplify the ultrasonic vibration amplitude.

Figures 2, 3:
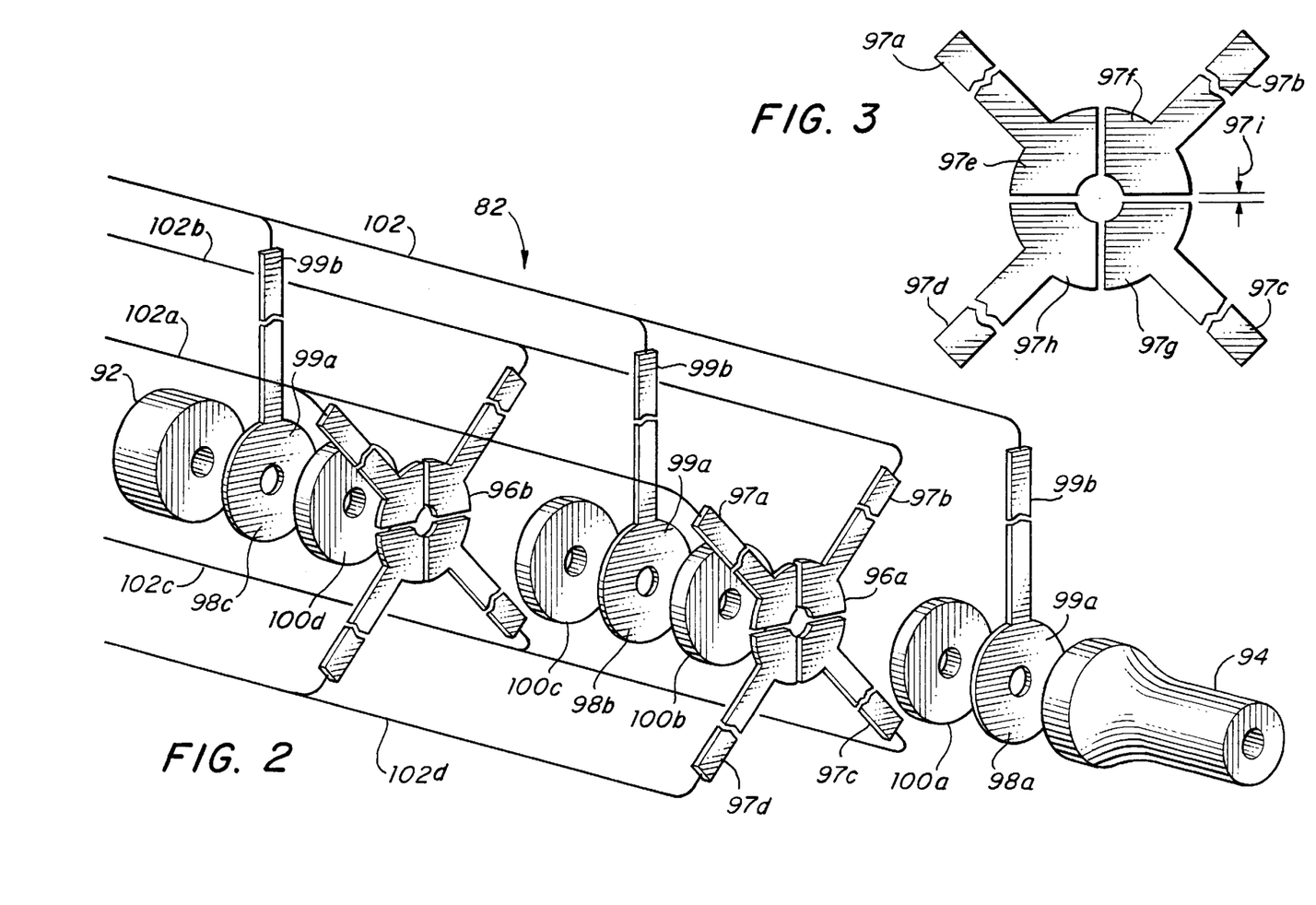
FIG. 2 is an exploded perspective view of a transducer assembly of the surgical system of FIG. 1.
FIG. 3 is a side elevational view of a segmented electrode.

As shown in FIG. 2, the transduction portion 90 of the transducer assembly 82 preferably comprises a piezoelectric section of alternating segmented electrodes 96a and 96b and negative electrodes 98a, 98b, and 98c, with piezoelectric elements 100a, 100b, 100c and 100d alternating between the electrodes 96a, 96b, 98a, 98b, and 98c. The piezoelectric elements 100a, 100b, 100c, and 100d may be fabricated from any suitable material, such as, for example, lead zirconate-titanate, lead meta-niobate, lead titanate, or other ceramic piezoelectric crystal material. Each of the segmented electrodes 96a and 96b, negative electrodes 98a, 98b, and 98c, and piezoelectric elements 100a, 100b, 100c, and 100d may have a bore extending through the center.

The negative electrodes 98a, 98b, and 98c of the transducer assembly 82 disposed between the piezoelectric element 100a and the resonator 94, the two inner piezoelectric elements 100b and 100c, and the piezoelectric element 100d and the resonator 92, respectively. The negative electrodes 98a, 98b, and 98c preferably have contact regions 99a and an input lead 99b. The contact regions 99a are preferably substantially circular. The input leads 99b of the negative electrodes 98 are coupled to a wire 102 that transmits electrical signals from the transducer control circuitry, as further described below, to the negative electrodes 98a, 98b, and 98c.

Referring now to FIG. 3, a side elevational view of a segmented electrode is shown. The segmented electrode has input leads 97a, 97b, 97c, 97d and contact regions 97e, 97f, 97g, 97h. The contact regions 97e, 97f, 97g, 97h of the segmented electrode are disposed on a selected portion of one or more of the piezoelectric elements. The contact regions 97e, 97f, 97g, 97h are separated by a dielectric gap 97i. Each of the input leads 97a, 97b, 97c and 97d of the segmented electrode is coupled to wires 104a, 104b, 104c, and 104d, respectively. The wires 104a, 104b, 104c, and 104d are coupled to corresponding transducer control circuitry, as further described below, to transmit electrical signals to the segmented electrode 96a of the transducer assembly 82.

The segmented electrodes allow the electrical signals transmitted to the transducer assembly to be distributed among one or more quadrants (i.e., 1 to 4) of the piezoelectric elements. The current distribution in each quadrant can be sensed and/or adjusted to generate a substantially uniform electric field or current density across the piezoelectric elements as further described below. It is contemplated that the segmented electrodes may have any suitable number of contact regions that may apply an electrical signal to a portion of one or more piezoelectric elements.

Referring again to FIG. 1, the piezoelectric elements are held in compression between the first and second resonators 92 and 94 by a bolt 106. The bolt 106 preferably has a head, a shank, and a threaded distal end. The bolt 106 is inserted from the proximal end of the first resonator 92 through the bores of the first resonator 92, the electrodes 96 and 98 and piezoelectric elements 100. The threaded distal end of the bolt 106 is screwed into a threaded bore in the proximal end of second resonator 94.

The mounting device 84 of the acoustic assembly 80 has a proximal end, a distal end, and may have a length substantially equal to an integral number of one-half system wavelengths. The proximal end of the mounting device 84 is preferably axially aligned and coupled to the distal end of the second resonator 94 by an internal threaded connection at or near an anti-node. (For purposes of this disclosure, the term "near" is defined as "exactly at" or "in close proximity to".) It is also contemplated that the mounting device 84 may be attached to the second resonator 94 by any suitable means, and that the second resonator 94 and the mounting device 84 may be formed as a single or unitary component.

The mounting device 84 is connected or mounted to the housing 52 of the handpiece assembly 50 near a node. The mounting device 84 may include an integral ring 108 disposed around its periphery. The integral ring 108 is preferably disposed in an annular groove 110 formed in the housing 52 of the handpiece assembly 50 to mount the mounting device 84 to the housing 52. A compliant member or material 112, such as a pair of silicone O-rings attached by stand-offs, may be placed between the annular groove 10 of the housing 52 and the integral ring 108 of the mounting device 86 to reduce or prevent ultrasonic vibration from being transmitted from the mounting device 84 to the housing 52.

The mounting device 84 may be secured in a predetermined axial position by a plurality of pins 114, preferably four. The pins 114 are disposed in a longitudinal direction 90 degrees apart from each other around the outer periphery of the mounting device 84. The pins 114 are coupled to the housing 52 of the handpiece assembly 50 and are disposed through notches in the integral ring 108 of the mounting device 84. The pins 114 are preferably fabricated from stainless steel. The mounting device 84 is preferably configured to amplify the ultrasonic vibration amplitude that is transmitted through the acoustic assembly 80 to the distal end of the end effector 88. In one preferred embodiment, the mounting device 84 comprises a solid, tapered horn. As ultrasonic energy is transmitted through the mounting device 84, the velocity of the acoustic wave transmitted through the mounting device 84 is amplified. It is contemplated that the mounting device 84 may be any suitable shape, such as, for example, a stepped horn, a conical horn, an exponential horn, a unitary gain horn or the like.

The distal end of the mounting device 84 is coupled to the proximal end of the transmission rod 86. It is contemplated that the transmission rod 86 be attached to the mounting device 84 by any suitable means, such as, for example, an internal threaded connection. The mounting device 84 is preferably coupled to the transmission rod 86 near an antinode.

The transmission rod 86 may, for example, have a length substantially equal to an integral number of one-half system wavelengths (nλ/2). The transmission rod 86 may be preferably fabricated from a solid core shaft constructed out of material which propagates ultrasonic energy efficiently, such as titanium alloy (i.e., Ti-6AI-4V) or an aluminum alloy. It is contemplated that the transmission rod 86 may be fabricated from any other suitable material. The transmission rod 86 may also amplify the mechanical vibrations transmitted through the transmission rod 86 to the end effector 88 as is well known in the art.

As illustrated in FIG. 1, the transmission rod 86 may include stabilizing silicone rings or compliant supports 116 positioned at a plurality of nodes. The silicone rings 116 dampen undesirable vibration and isolate the ultrasonic energy from a removable sheath 120 assuring the flow of ultrasonic energy in a longitudinal direction to the distal end of the end effector 88 with maximum efficiency.

As shown in FIG. 1, the removable sheath 120 is coupled to the distal end 56 of the handpiece assembly 50. The sheath 120 generally includes an adapter or nose cone 122 and an elongated tubular member 124. The tubular member 124 is attached to the adapter 122 and has an opening extending longitudinally therethrough. The sheath 120 may be threaded or snapped onto the distal end of the housing 52. The transmission rod 86 of the acoustic assembly 80 extends through the opening of the tubular member 124 and the silicone rings 116 isolate the transmission rod 86 therein.

The adapter 122 of the sheath 120 is preferably constructed from Ultem®, and the tubular member 124 is fabricated from stainless steel. Alternatively, the transmission rod 86 may have polymeric material that surrounds the transmission rod 86 to isolate it from outside contact.

The distal end of the transmission rod 86 may be coupled to the proximal end of the end effector 88 by an internal threaded connection, preferably at or near an antinode. It is contemplated that the end effector 88 may be attached to the transmission rod 86 by any suitable means, such as a welded joint or the like. Although the end effector 88 may be detachable from the transmission rod 86, it is also contemplated that the end effector 88 and transmission rod 86 may be formed as a single unit.

The end effector 88 may have a distal region 88b having a smaller crosssection area than a proximal region 88a thereof, thereby forming a vibrational amplitude step-up junction. The step-up junction acts as velocity transformer as known in the art, increasing the magnitude of the ultrasonic vibration transmitted from the proximal region 88a to the distal region 88b of the end effector 88.

The end effector 88 may have a length substantially equal to an integral multiple of one-half system wavelengths (nλ2). The end effector 88 may be disposed at an antinode in order to produce the maximum longitudinal deflection of the distal end. When the transducer assembly 82 is energized, the distal end of the end effector 88 is configured to move longitudinally in the range of, for example, approximately 10 to 500 microns peak-to-peak, and preferably in the range of about 30 to 100 microns at a predetermined vibrational frequency, and most preferably at about 90 microns.

The end effector 88 is preferably made from a solid core shaft constructed of material which propagates ultrasonic energy, such as a titanium alloy (i.e., Ti-6AI-4V) or an aluminum alloy. It will be recognized that the end effector 88 may be fabricated from any other suitable material. It is also contemplated that the end effector 88 may have a surface treatment to improve the delivery of energy and desired tissue effect. For example, the end effector 88 may be micro-finished, coated, plated, etched, grit-blasted, roughened or scored to enhance coagulation in tissue and/or reduce adherence of tissue and blood to the end effector. Additionally, the end effector 88 may be sharpened or shaped to enhance its energy transmission characteristics. For example, the end effector 88 may be blade shaped, hook shaped, or ball shaped.

Figure 4:
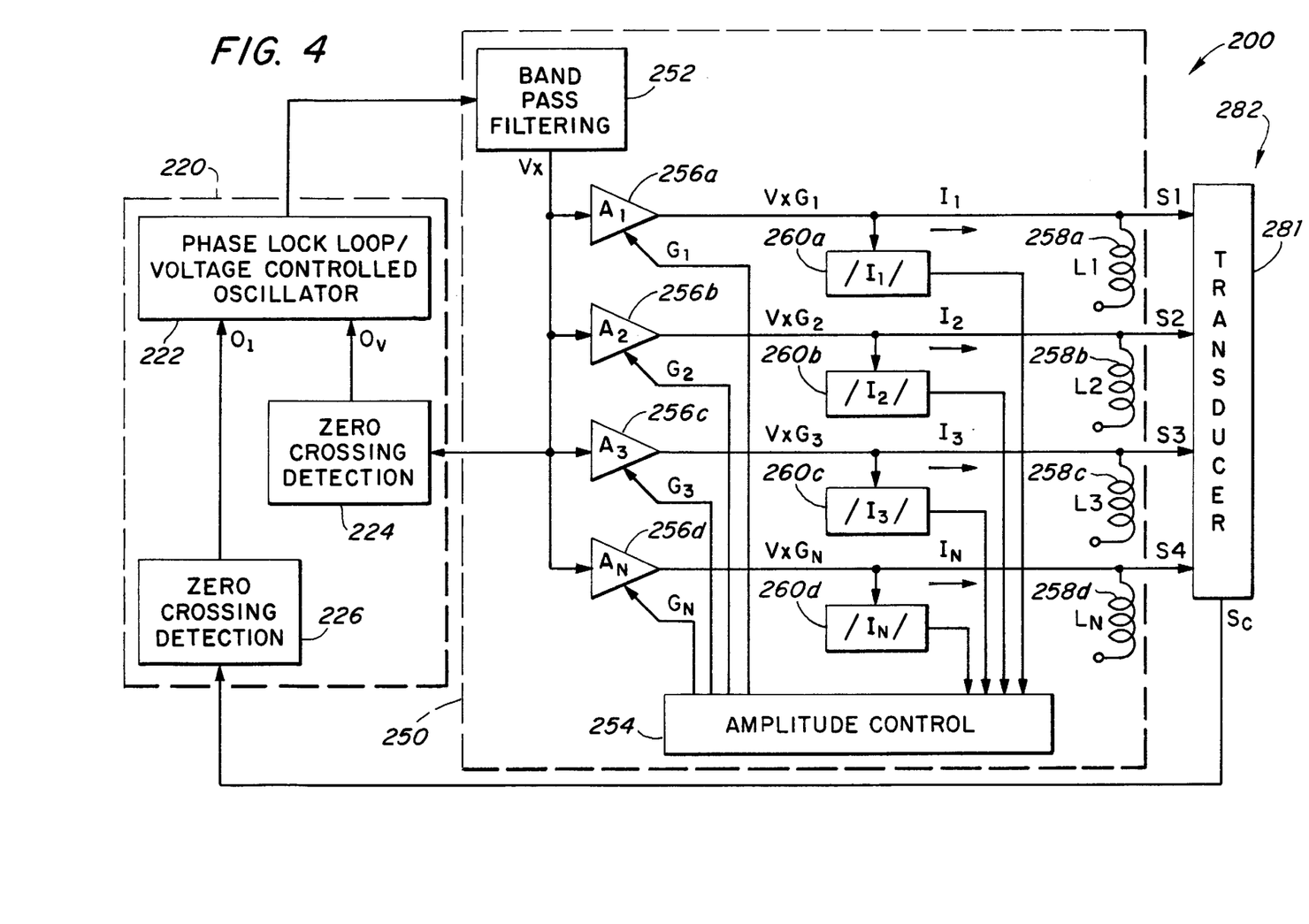
FIG. 4 is a block diagram of transducer control circuitry of the generator of FIG. 1.

Referring now to FIG. 4, a block diagram of the transducer control circuitry or drive circuitry 200 to excite one or more piezoelectric elements of a transducer assembly 282 is illustrated. The transducer control circuitry 200 provides electrical signals to drive the transducer assembly 282 at a desired frequency and power level setting.

The piezoelectric elements of the transducer assembly 282 are energized in response to electrical signals supplied from the transducer control circuitry 200. The electrical signals cause disturbances in the piezoelectric elements in the form of repeated small displacements resulting in large compression forces within the material. The repeated small displacements cause the piezoelectric elements to expand and contract in a continuous manner along the axis of the voltage gradient, producing high frequency longitudinal waves of ultrasonic energy. The ultrasonic energy may be transmitted to vibrate a distal end of an end effector.

The components 200 of the transducer control circuitry generally include a frequency control circuitry 220 and amplitude control circuitry 250. The frequency control circuitry 220 preferably includes a phase lock loop/voltage controlled oscillator 222, a voltage zero crossing detector 224, and a current zero crossing detector 226.

Figure 5:
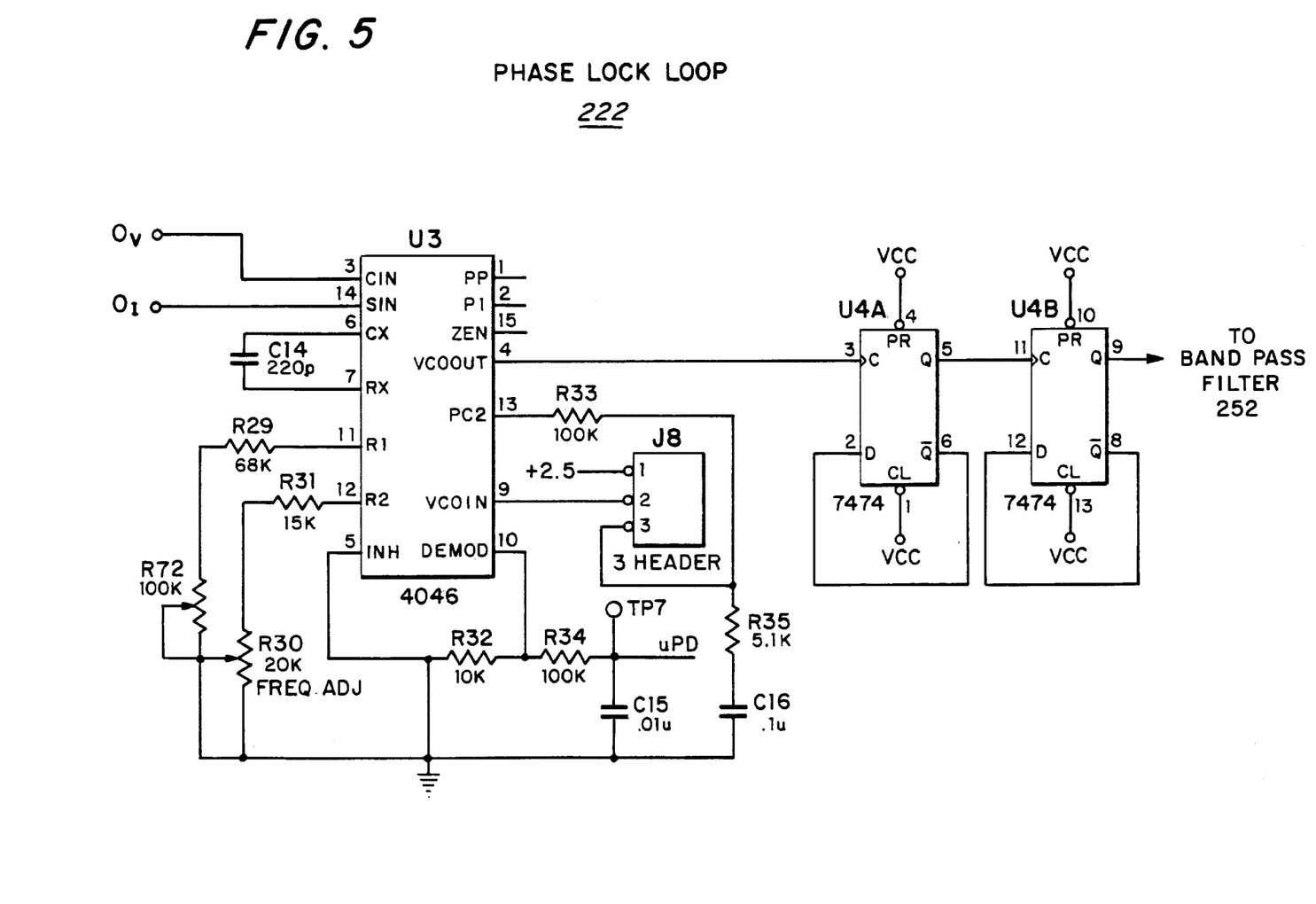
FIG. 5 is a circuit diagram of a phase lock loop of the transducer control circuitry of FIG. 4.

The phase lock loop 222 of the frequency control loop 220 adjusts the frequency of the electrical signals to match a preselected harmonic frequency of the transducer assembly 282. The phase lock loop 222 receives a phase voltage signal $O_v$ from the voltage zero crossing detection circuit 224 and a phase current signal $O_I$ from the current crossing detector 226. The phase voltage signal $O_v$ and phase current signal $O_I$ allows the phase lock loop 222 to maintain resonance with the transducer assembly 282. An exemplary circuit diagram of the phase lock loop 222 is illustrated in FIG. 5.

Figure 6:
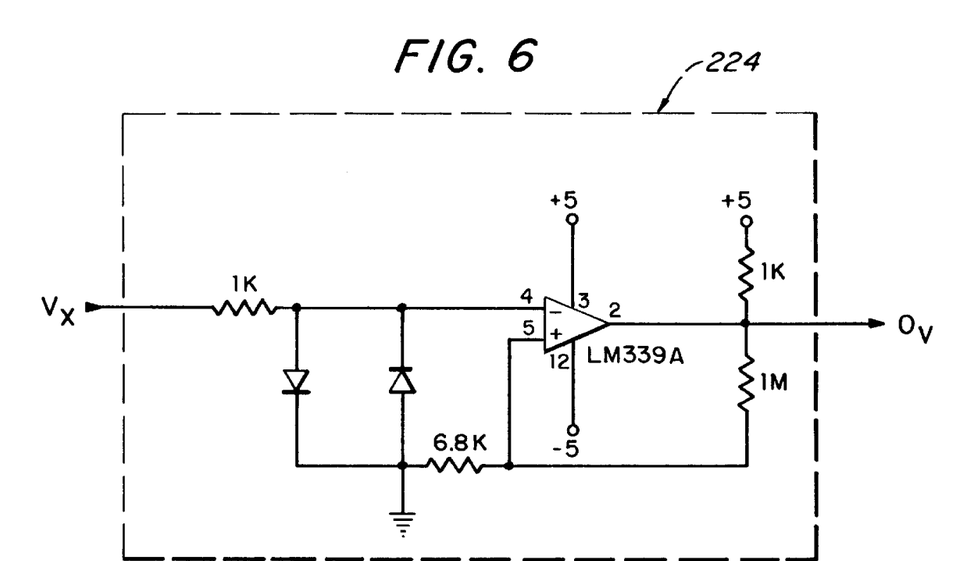
FIG. 6 is a circuit diagram of a zero voltage crossing detector of the transducer control circuitry of FIG. 4.

As shown in FIG. 4, the voltage zero crossing detector 224 of the frequency control loop 220 receives an input signal from band pass filtering circuitry 252 of the amplitude control circuitry. The voltage zero crossing detector 224 detects when the voltage signal transitions through zero volts and outputs a pulse that conveys the phase voltage signal $O_v$ to the phase lock loop 222. The voltage zero crossing detector 224 is preferably a LM339A comparator available from National Semiconductor. An exemplary circuit diagram of the voltage zero crossing detector is illustrated in FIG. 6. It is also contemplated that the voltage zero crossing detector may be derived from the input of the Band Pass filter.

Figure 7:
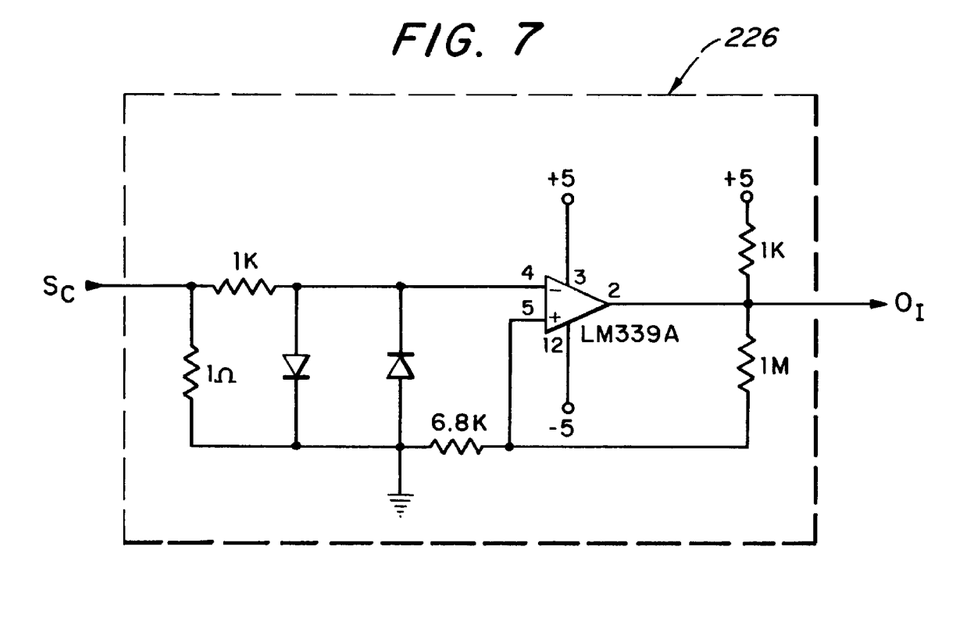
FIG. 7 is a circuit diagram of a zero current crossing detector of the transducer control circuitry of FIG. 4.

The current zero crossing detector 226 of the frequency control loop 220 receives an input signal Sc from the transducer assembly 282. The current zero crossing detector 226 detects when the current signal transitions through zero amperes and outputs a pulse that conveys a phase current signal 01 to the phase lock loop 222. The current zero crossing detector 226 is preferably a LM339A comparator available from National Semiconductor. An exemplary circuit diagram of the zero crossing detector 226 is illustrated in FIG. 7.

The amplitude control circuitry 250 of the drive circuitry 200 maintains the electrical signals supplied to the transducer assembly 282 at a preselected constant level in order to achieve substantially constant vibrational amplitude at the distal end of the acoustic assembly. The amplitude control circuitry 250 preferably includes a band pass filter 252, an amplitude control device 254, amplifiers 256a, 256b, 256c, 256d, inductors 258a, 258b, 258c, 258d, and current sensors 260a, 260b, 260c, 260d.

The band pass filter 252 of the amplitude control circuitry 250 receives the output signal from the phase lock loop 222 of the frequency control circuitry 220. The band pass filter removes the non-fundamental frequency components from the input square wave and converts the input into a sine wave. The band pass filter 252 generates an output signal $V_x$, that is transmitted to the amplifiers 256a, 256b, 256c, 256d. The band pass filter 252 is preferably a tuned passive L/C network or active filter.

The amplifiers 256a, 256b, 256c, 256d of the amplitude control circuit 250 send drive or electrical signals to the piezoelectric elements of the transducer assembly 282. The drive signals can be varied to control of the amplitude of vibration of selected portions or segments of the piezoelectric elements. Each amplifier 256a, 256b, 256c, 256d receives an output signal $V_x$ from the band pass filtering circuit 252 and also receives a respective gain signal G1, G2, G3, G4 from the amplitude control device 254. The amplifiers 256a, 256b, 256c, 256d generate output signals $V_xG_1$, $V_xG_2$, $V_xG_3$, $V_xG_4$ respectively. The output signals are applied to a respective electrode to excite the piezoelectric elements of the transducer assembly 282.

Figure 8:
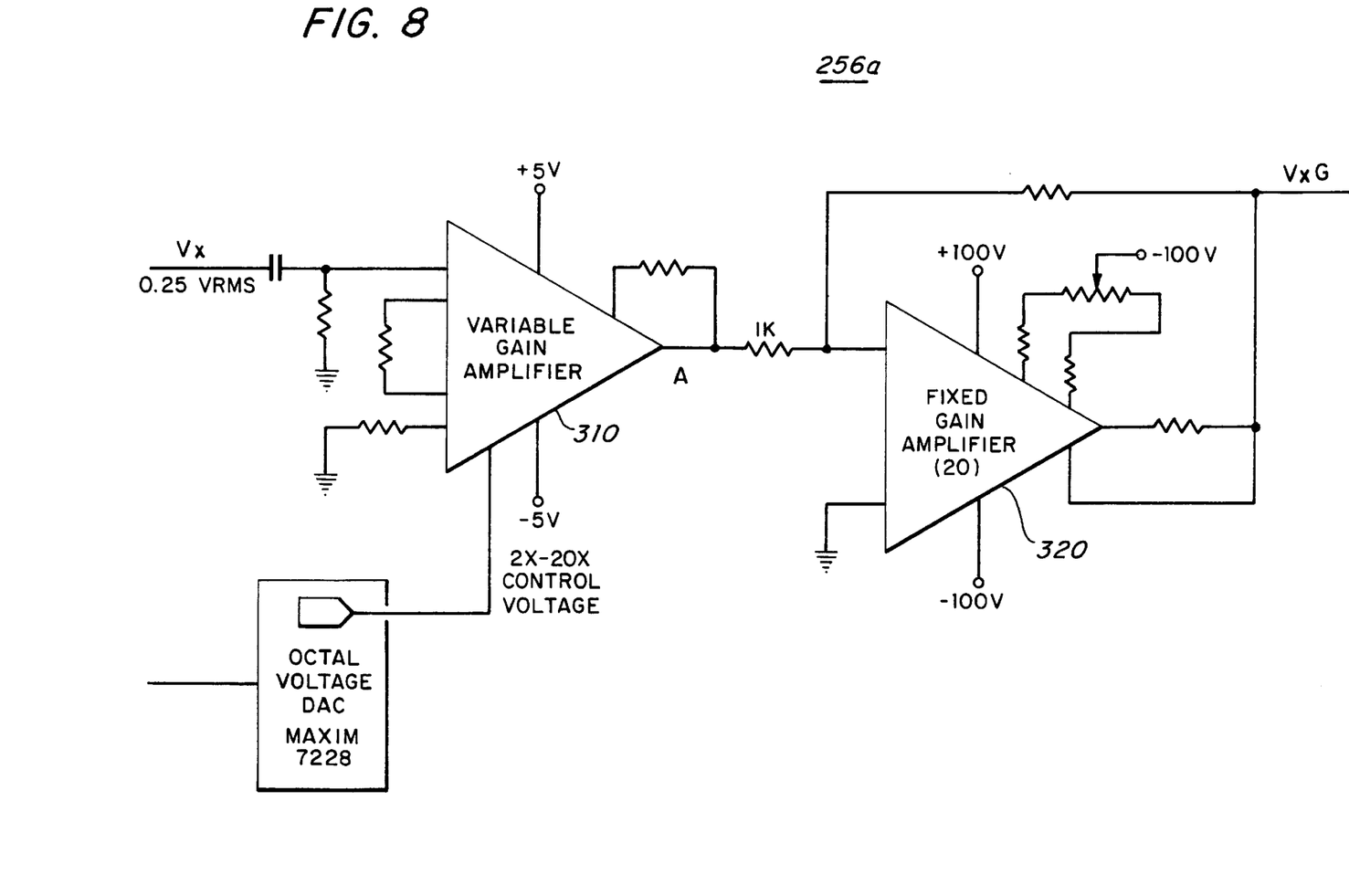
FIG. 8 is a circuit diagram of an amplitude control of the transducer control circuitry of FIG. 4.
Figure 9:
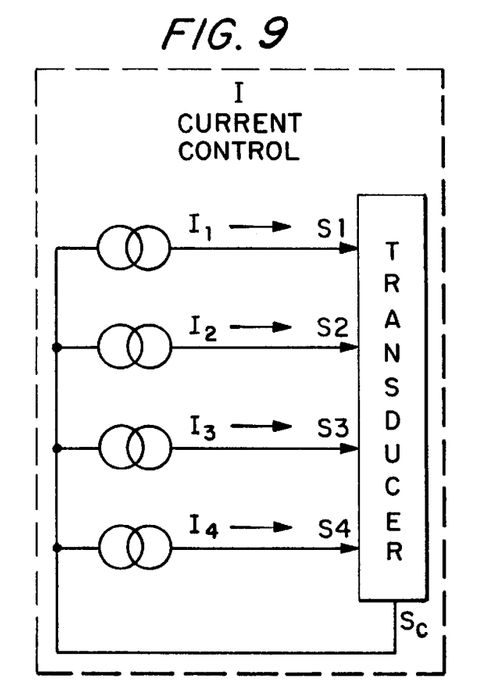
FIG. 9 is a simplified block diagram of the amplitude control portion of the transducer control circuitry of FIG. 4.
Figure 10:
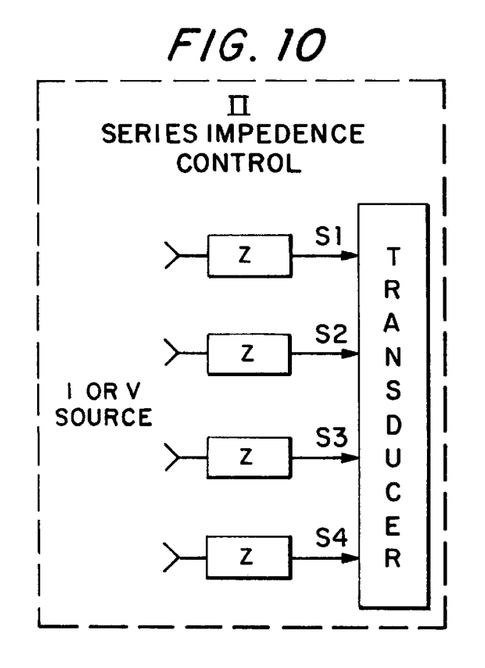
FIG. 10 is a simplified block diagram of an alternative for amplitude circuitry control of the transducer control circuitry of FIG. 4.
Figure 11:
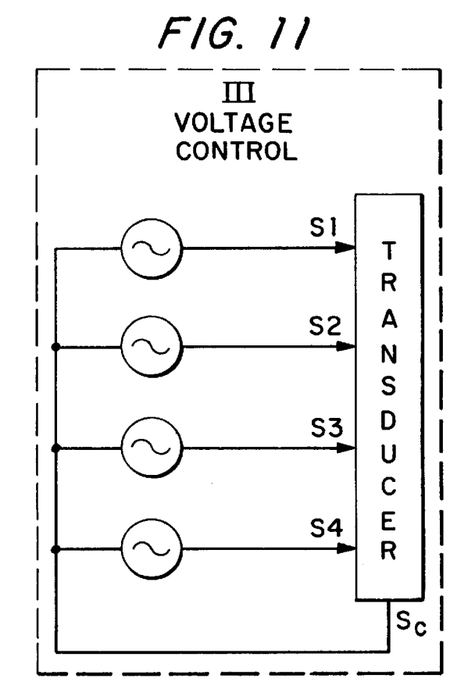
FIG. 11 is a simplified block diagram of an alternative for amplitude control circuitry of the generator of FIG. 4.
Figure 12:
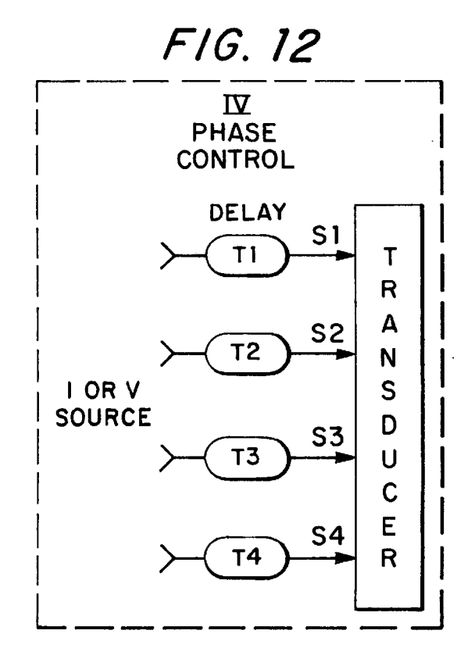
FIG. 12 is a simplified block diagram of an alternative for amplitude control of the transducer control circuitry of FIG. 4.

Referring now to FIG. 8, a circuit diagram of the amplifier 256a is illustrated. The amplifier 256a includes a variable gain amplifier 310 and a fixed gain amplifier 320. The variable gain amplifier 310 receives an input signal Vx and amplifies the signal Vx. The variable gain amplifier 310 generates an amplified signal A that is transmitted to the constant or fixed gain amplifier 320. The gain of the amplified signal Vx is controlled by the amplitude control device 254.

The constant gain amplifier 320 receives the amplified signal A and amplifies the signal. The constant gain amplifier 320 amplifies the signal based upon the following equation:

$$20 \cdot A$$

The constant gain amplifier 320 outputs a signal which is provided to the transducer assembly. It will be recognized that the amplifiers 256b, 256c, and 256d circuitry are substantially similar to the circuitry of the amplifier 256a.

The current sensors 260a, 260b, 260c, 260d of the amplitude control circuit 250 are used to monitor the current in each segment of the piezoelectric elements in order to detect current imbalances which can indicate non-fundamental modes of vibration. The current sensors 260a, 260b, 260c, 260d receive output signals $V_xG_1$, $V_xG_2$, $V_xG_3$, $V_xG_4$ from the amplifier circuitry 256a, 256b, 256c, 256d, respectively, and send an output signal to the amplitude control device 254. The current sensors 260a, 260b, 260c, 260d are preferably operational amplifiers implementing a RMS to DC conversion.

The amplitude control device 254 of the amplitude control circuitry 250 receives a signal from the current sensors 260a, 260b, 260c, 260d. The amplitude control device 254 can sense uneven current flow and compensate from the uneven current flow by varying the gains of the amplifies 256a, 256b, 256c, 256d. As a result, the amplitude of the drive voltages of the amplifies 256a, 256b, 256c, 256d can be modified to apply a desired signal to piezoelectric elements of the transducer. It is also contemplated that the amplitude and/or phase of the drive signals $V_xG_1$, $V_xG_2$, $V_xG_3$, $V_xG_4$ can be varied to control the vibration of the piezoelectric elements. The amplitude control device may be carried out by a microprocessor, such as, for example, a 68HC11 microprocessor.

The inductors 258a, 258b, 258c, 228d of the amplitude control circuit 250 are coupled between the output voltages $V_xG_1$, $V_xG_2$, $V_xG_3$, $V_xG_4$ and ground. Inductors 258a, 258b, 258c, 258d are used to compensate for the effective capacitance of each segment of the piezoelectric elements. The inductors 258a, 258b, 258c, 228d are preferably about 10 mH, 10 mH, 10 mH, and 10 mH, respectively.

Referring now to FIGS. 9–12, alternative embodiments for controlling the drive signals to a transducer assembly are shown. The transducer assembly may be driven by controlling current (FIG. 9), impedance (FIG. 10), voltage (FIG. 11), phase (FIG. 12) or any combination thereof. When controlling the transducer assembly through impedance or phase control, a current or voltage source may be utilized.

The devices and methods in accordance with the present invention are provided to dampen undesired vibration of transmission members. The devices and method can sense undesired frequencies of vibration, such as non-fundamental modes, in piezoelectric elements of a transducer and control the electrical field distributed across the piezoelectric elements to reduce undesired vibration of the transmission components. The electrical properties, such as the current, voltage, impedance, and phase, of the piezoelectric elements of the transducer can be continuously sensed in order to provide a desired vibrational frequency.

The devices and methods can also sense non-fundamental modes of vibration. The device and method can also introduce non-fundamental modes to optimize acoustic system performance. The introduction of non-fundamental modes allows more efficient delivery of power at the fundamental transducer frequency. In addition, the non-fundamental mode can be utilized to enhance tissue effects.

The devices and methods allow longer and narrower transmission components (i.e., blades) to be utilized. Furthermore, the devices and methods allow mechanical dampening to be reduced, resulting in increased efficiency of the ultrasonic energy transmitted to the transmission component. The devices and methods also increase life expectancy of the transmission components.

Although the present invention has been described in detail by way of illustration and example, it should be understood that a wide range of changes and modifications can be made to the preferred embodiments described above without departing in any way from the scope and spirit of the invention. Thus, the described embodiments are to be considered in all aspects only as illustrative and not restrictive, and the scope of the invention is, therefore, indicated by the appended claims rather than the foregoing description. All changes that come within the meaning and range of equivalency of the claims are to be embraced within their scope.

What is claimed is:

1. A generator to drive at least one transducer element comprising:

a phase lock loop;

a zero crossing detector coupled to the phase lock loop;

a filtering device coupled to the phase lock loop and to a plurality of amplifiers;

the plurality of amplifiers generating a plurality of signals to drive the at least one transducer element; and a control device coupled to each of the plurality of amplifiers to adjust the gain of the amplifiers.

2. The generator of claim 1 further comprising a plurality of sensors coupled to a respective output of the plurality of amplifiers to detect the drive signal.

3. The generator of claim 1 wherein the drive signal comprises one of a voltage signal, current signal, impedance signal, and phase signal.

4. The generator of claim 1 further comprising a plurality of inductors coupled to a respective output of the amplifiers.

5. A method of driving at least one transducer element comprising the steps of:

i) providing a phase lock loop;

ii) providing a zero crossing detector coupled to said phase lock loop;

iii) providing a filtering device coupled to said phase lock loop and to a plurality of amplifiers; said plurality of amplifiers generating a plurality of signals to drive the at least one transducer element; and iv) providing a control device coupled to each of said plurality of amplifiers to adjust the gain of said amplifiers.

6. The method of claim 5 further comprising the step of providing a plurality of sensors coupled to the respective outputs of said plurality of amplifiers to detect the drive signal.

7. The method of claim 6 wherein said drive signal comprises one of a voltage signal, current signal, impedance signal, and phase signal.

8. The method of claim 6 further comprising the step of providing a plurality of inductors, each coupled to a respective output of said amplifiers.

* * * * *